United States Patent [19]

Randklev

[11] Patent Number: 5,015,180
[45] Date of Patent: May 14, 1991

[54] DENTAL ARTICLE CONTAINING LIGHT-CURABLE PASTE

[75] Inventor: Ronald M. Randklev, Grand Marais, Minn.

[73] Assignee: Minnesota Mining and Manufacturing Company, St. Paul, Minn.

[21] Appl. No.: 317,651

[22] Filed: Mar. 1, 1989

[51] Int. Cl.⁵ .............................................. A61C 3/00
[52] U.S. Cl. ...................................... 433/9; 433/215; 433/226; 433/228.1
[58] Field of Search ............... 433/9, 217.1, 39, 228.1, 433/40, 215, 226

[56] References Cited

U.S. PATENT DOCUMENTS

| | | |
|---|---|---|
| 2,659,970 | 11/1953 | Ignersoll, Jr. |
| 2,835,628 | 5/1958 | Saffir |
| 3,250,003 | 5/1966 | Collito |
| 3,265,202 | 8/1986 | Cornell ............... 206/63.5 |
| 3,504,438 | 4/1970 | Wittman et al. |
| 3,708,379 | 1/1973 | Flint ........................ 161/36 |
| 3,729,313 | 4/1973 | Smith ....................... 96/27 R |
| 3,741,769 | 6/1973 | Smith ....................... 96/35.1 |
| 3,797,115 | 3/1974 | Silverman et al. |
| 3,837,981 | 9/1974 | Flint ........................ 161/36 |
| 4,063,360 | 12/1977 | Waller ....................... 433/9 |
| 4,091,157 | 5/1978 | Hori et al. .................. 428/196 |
| 4,094,068 | 6/1978 | Schinhammer |
| 4,117,596 | 6/1978 | Wallshein |
| 4,179,812 | 12/1979 | White ......................... 433/9 |
| 4,204,325 | 5/1980 | Kaelble ....................... 433/9 |
| 4,211,021 | 7/1980 | Amprim et al. .............. 40/628 |
| 4,243,462 | 1/1981 | Hori et al. ................. 156/310 |
| 4,394,403 | 7/1983 | Smith ......................... 427/42 |
| 4,479,782 | 10/1984 | Orlowski et al. ............. 433/9 |
| 4,503,169 | 3/1985 | Randklev ................. 433/228.1 |
| 4,695,251 | 9/1987 | Randklev .................... 433/9 |
| 4,718,849 | 1/1988 | von Weissenfluh et al. .... 433/39 |
| 4,728,291 | 3/1988 | Golub ....................... 433/215 |
| 4,749,352 | 6/1988 | Nicholson .................... 433/9 |

FOREIGN PATENT DOCUMENTS 0290133 11/1988 European Pat. Off.
1428674 3/1976 United Kingdom ............. 433/13

OTHER PUBLICATIONS

Richard F. Ceen, "Orthodontic Bonding—An Overview", *The Journal of Pedodontic,* Fall 1980, pp. 62–71.

*Primary Examiner*—Cary E. Stone
*Attorney, Agent, or Firm*—Wegner, Cantor, Mueller & Player

[57] ABSTRACT

A dental tape is disclosed comprising a light-curable, non-toxic paste layered between two cover sheets, at least one of which releasably adheres to the paste, and a dental article is disclosed comprising an orthodontic bracket having a base and a light-curable, non-toxic paste sandwiched between the base and a releasably adhering substrate.

33 Claims, 1 Drawing Sheet

DENTAL ARTICLE CONTAINING LIGHT-CURABLE PASTE

The present invention relates to a dental tape having a curable paste sandwiched between two cover sheets. The present invention also relates to an orthodontic bracket having a layer of curable paste thereon acting as an adhesive.

Curable pastes useful as restorative materials and adhesives for orthodontic brackets are known. However, use of such pastes often requires painstaking measurement of components and mixing by the dental practitioner. Further, the practitioner must carefully determine the minimum amount of paste necessary for bonding in order to avoid excess adhesive around the bracket, which would require further time consuming removal in order to eliminate an undesirable site for plaque accumulation. Furthermore, many known pastes have the disadvantage of having to be activated outside the mouth, before application, thereby reducing available working time inside the mouth; once the paste was activated, the practitioner had little time to work the paste, e.g., into a suitable restoration element. U. S. Pat. No. 4,204,325 discloses an orthodontic bracket having a curable paste layer applied thereto, which is covered by a releasable film. After removing the film, and prior to placement of the bracket on the tooth, the paste layer is activated by surface application of a curing agent. Since activation occurs outside the mouth, the practitioner is given little time to position the bracket at the precise location desired on the tooth surface.

Accordingly, the present invention is a dental tape comprising a light-curable, non-toxic paste layered between two cover sheets, at least one of which releasably adheres to the paste. The present invention is also a dental article comprising an orthodontic bracket having a base adapted to adhere to a tooth surface and a light-curable non-toxic paste sandwiched between the base and a releasably adhering substrate.

Figure 1:
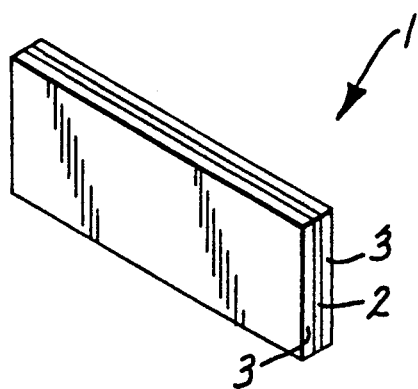
FIG. 1 is an end elevational view of the tape of the present invention.

A tape of the present invention is useful in restorative applications, such as cosmetic veneers, veneers to mask severely stained teeth, cervical erosion repair, a desensitizing cover for sensitive teeth, a fiber reinforced splint or lay-up tape for chemical crowns and denture molds, a matrix strip to be formed cured, and then filled with a dental restorative, or an orthodontic bracket adhesive tape.

Light-curable, non-toxic pastes useful in accordance with the present invention preferably contain a photoinitiator and a filler dispersed in a resin. Useful resins are hardenable, organic compounds having sufficient strength, hydrolytic stability, and non-toxicity to render them suitable for use in the mouth. Examples of such resins include acrylate, methacrylate, urethane, and epoxy resins, such as disclosed in U.S. Pat. Nos. 3,066,112, 3,539,533, 3,629,187, 3,709,866, 3,751,399, 3,766,132, 3,860,556, 4,002,669, 4,115,346, 4,259,117, 4,292,029, 4,306,190, 4,327,014, 4,379,695, 4,387,240, and 4,404,150, the disclosures of which are incorporated herein by reference. Mixtures and derivatives of such resins are also useful. Preferably, the resin is a mixture of diglycidylmethacrylate of Bisphenol A ("Bis-GMA") and triethyleneglycol dimethacrylate ("TEGDMA"). Useful photoinitiators are non-toxic compounds, such as ketone or alpha-diketone compounds, alone or in combination with suitable amines, peroxides, sulfur compounds, phosphorus compounds, or other compounds capable of reacting with or being sensitized by the ketone or alpha-diketone compounds to effect polymerization of the resin. Preferred photoinitiators include a mixture of dl-camphorquinone and dimethylaminophenethanol ("DMAPE"), and photoinitiator systems such as disclosed in European Pat. Application No. 0290133, the disclosure of which is incorporated herein by reference. Suitable fillers for oral use are well known, such as disclosed in U.S. Pat. Nos. 4,695,251 and 4,435,160, the disclosures of which are incorporated herein by reference. Preferred fillers include quartz, radiopaque glass, and non-vitreous microparticles as disclosed in U.S. Pat. No. 4,503,169, the disclosure of which is incorporated herein by reference. The microparticles are particularly advantageous in pastes intended for anterior restorations since they provide a cured composite paste having a low visual opacity. Other preferred fillers include low hardness minerals such as kaolinite, mica, pyrophyllite, and talc.

The paste is preferably prepared in the absence of light by first combining the resin and photoinitiator and then adding the filler. In some applications, absence of occluded air from the paste is desirable, e.g., in matrix composites and bracket adhesives. Accordingly, the paste is preferably mixed under partial vacuum as well.

The paste contains a filler and optional pigment to produce varying degrees of opacity as desired. Optionally, the paste is fiber or fiber scrim reinforced for applications such as splinting. Useful fiber types include glasses, such as electrical grade glass, and ceramics. Useful scrims have various yarn types, identified by the number of filaments per yarn, the number of yarns per inch in both warp (machine) and fill (transverse) directions, and the weave style.

Optionally, the paste includes suitable adjuvants such as accelerators, inhibitors, stabilizers, pigments, dyes, viscosity modifiers, extending or reinforcing fillers, surface tension depressants and wetting aids, or anti-oxidants. Particularly useful optional ingredients include colloidal silica thickeners, which help provide an optimum viscosity for the paste, and may permit higher amounts of filler loading needed for particular applications.

Amounts of components used in the paste vary depending on particular ingredients used as well as the intended application. Generally the resin/filler ratio is adjusted to provide a sufficient consistency to the paste to permit easy handling and prevent slump. Generally, more heavily loaded pastes provide more visually opaque cured products. The amount of photoinitiator used is generally an amount sufficient to cure the resin after a brief exposure to a curing light. For general applications, the paste preferably comprises 10–40% resin 60–90% filler and 0.1–5.0% more preferably 0.1–1.0%, photoinitiator. The thickness of the paste layer is adjustable by the skilled artisan depending on specific applications, with preferred thickness varying between about 0.2 and 1.3 mm.

The tape of the present invention contains the paste sandwiched between two cover sheets, at least one of which removably adheres to the paste. As shown in FIG. 1, dental tape 1 contains paste 2 sandwiched between flexible cover sheets 3. Removably adhering cover sheets are preferably "hand hard" (i.e., resilient) films made of polyester, fluorinated polymers such as polytetrafluoroethylene, or olefin polymers such as polypropylene or polyethylene. More preferably, the removably adhering cover sheet has a low-adhesion backsize coating applied on the surface contacting the paste for ease of removal of the tape. Such low-adhesion backsize coatings include silicone coatings and polytetrafluoroethylene coatings, which are well known to those skilled in the art. Preferably, the thickness of the removably adhering cover sheet is between about 0.00635 and 0.0127 mm. In applications where both cover sheets are removed before curing the paste, e.g., bracket adhesives, both cover sheets of the tape removably adhere to the paste.

For use in restorative applications and as matrix tapes, one of the cover sheets preferably remains on the paste until it is cured. Accordingly, the remaining cover sheet is preferably transparent to light of the desired curing wavelength to allow optimum curing of the paste. For matrix tape applications, the transparent cover sheet is preferably a "dead-soft" or "hand-soft" (i.e., non-resilient) film, such as polyvinylidene chloride. Other useful hand-soft films will be readily apparent to those of ordinary skill in the art. The thickness of the transparent cover sheet preferably varies between about 0.0127 and 0.508 mm, more preferably between about 0.0178 and 0.0254 mm. Thin cover sheets are particularly useful when the transparent sheet must fit between adjacent teeth, such as in splinting and matrix banding.

Methods of making the tape of the present invention include pattern coating, knife coating, reverse roll coating, nip roll coating, and other methods that will be apparent to those in the art.

For an orthodontic bracket adhesive, disposed either in a tape or on an orthodontic bracket according to the present invention, the paste preferably contains 10–70% resin and 30–90% filler by weight of the paste. Precise amounts, determinable by the skilled artisan, vary depending on the particular components used as well as the bracket composition. In an adhesive tape, the paste has a preferable thickness between 0.245 and 0.508 mm. The filler preferably has a Mohs hardness less than about 4, more preferably less than about 3. These preferred values for Mohs hardness ensure a filler that is less hard than either natural tooth enamel or the typical abrasive materials used for adhesive removal, thus facilitating removal of the adhesive after the orthodontic bracket is removed at the termination of treatment while minimizing enamel damage. When used as a bracket adhesive, the consistency of the paste is preferably adjusted to provide the desired mechanical retention of the paste on the bracket as well as to allow good mesh penetration and flow around the screen wires of both 60 and 100 mesh screen bases of orthodontic brackets.

In one embodiment of the present invention, an orthodontic bracket is provided with a layer of light-curable adhesive sandwiched between the base of the bracket and a releasably adhering substrate. Preferably, the substrate is a flexible cover sheet, such as the removably adhering cover sheets described herein.

Figure 2:
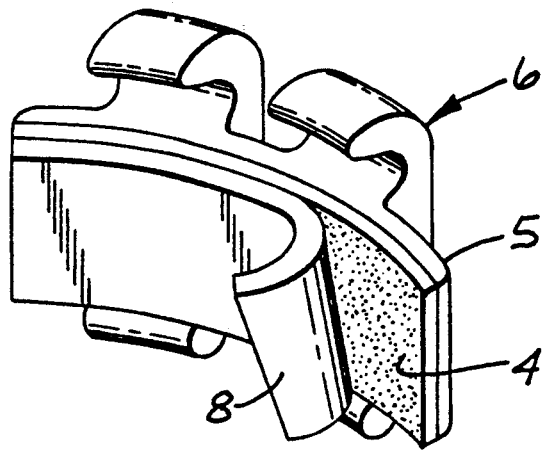
FIG. 2 is an end elevational view of a preferred embodiment of the adhesive-coated orthodontic bracket of the present invention.

Referring to FIG. 2, paste layer 4 is provided between base 5 of bracket 6 and cover sheet 8. To obtain the embodiment shown in FIG. 2, for example, after removing a releasably adhering cover sheet (not shown in FIG. 2), the cover sheet-backed adhesive is pressed onto the base between press platens or nip rolls with predetermined pressure sufficient to provide penetration of mesh screens or perforations, where present. Preferably, the tape is first cut and shaped to correspond to the size of the bracket base before application thereto. Alternatively, the paste can also be applied to the bracket base and then covered by a removably adhering cover sheet.

To bond the bracket 6 to a tooth, the cover sheet 8 is then removed from the paste and the paste-covered bracket base applied to the tooth. A light source is then directed around the periphery of the bracket base, through the bracket itself if transparent to the curing light, or through the lingual side of the tooth for a sufficient time to cure the paste.

The present invention frees the practitioner from the need to dispense and apply an adhesive to an orthodontic bracket. Furthermore, adequate penetration of the adhesive into the bracket screen or perforations can be predetermined and ensured under manufacturing conditions, freeing the practitioner of this uncertainty. In addition, excess adhesive is minimized or eliminated, reducing the time normally required for clean-up.

Useful orthodontic brackets are well known in the art and are made from materials such as stainless steel, ceramics (e..g., polycrystalline alumina and sapphire) and transparent plastics. Typically, the bracket has bracket posts adapted for fastening arch wires that are attached to a base adapted to conform to the buccal or labial surface of the tooth. The bracket base may have an irregular surface adapted to receive the paste in such a way that, when cured, the paste anchors the bracket to the tooth surface. Examples of modified bracket bases are well known and include wire mesh screens fixed to the base as well as perforated and undercut bases. Most preferably, metal bracket bases are equipped with a wire mesh screen having, e.g., a 60 or 100 mesh size. To anchor a metal bracket securely to the tooth, the paste preferably penetrates the screen, flowing around the individual mesh wires. The paste layer provided on the bracket in accordance with the present invention has a preferable thickness between about 0.245 and 0.508 mm.

The dental tape of the present invention is also useful as a matrix band in place of metal matrix bands used in many Class II restorations. Utilizing the dental tape of the present invention allows for more precise shaping of the tape to the original contour of the tooth and for proper spacing in contact areas. Following placement of the matrix band around a tooth that was drilled to remove part of the side of the tooth, the paste covering the hole in the side of the tooth is cured using a curing light. The drilled area now enclosed by the remaining tooth structure and the cured paste is filled with a suitable restorative material, which is then cured, the entire restoration providing an integrally formed, matrix-tape restoration. After curing of the restoration, the transparent cover film is removed to reveal a fully cured and lustrous surface. Surface lustre may be adjusted by using cover films with various finishes, e.g., matte. Since the matrix tape can be made very thin, it can easily be wedged between adjoining teeth. The practitioner can also immediately determine the contact area between adjacent teeth and shape or compress the uncured matrix layer accordingly. For matrix tape applications, the resin amount is preferably between about 10–50%, more preferably 10–15%, based on the weight of the paste. The preferred amount of filler in matrix tape application is about 50-90%, more preferably 85-90%, based on the weight of the paste. For matrix tape applications, the thickness of the paste layer is preferably between about 0.127 and 0.254 mm. Since the matrix band is wound around the tooth surface, a minimal thickness is desired to allow ease of placement between the teeth.

The dental tape of the present invention is also useful as a veneer to replace lost, damaged, or discolored tooth enamel. When used as a veneer, the paste layer has a thickness between about 0.25 and 0.5 mm. For veneers, the resin amount is preferably between about 10-20%, more preferably 10-15%, based on the weight of the paste. The preferred amount of filler in veneers is about 80-90%, more preferably 85-90%, based on the weight of the paste. In repairing cervical erosion of teeth, several applications of tape may be necessary, depending on the thickness of the paste layer used and the depth of erosion.

and percentages in the examples are by weight unless indicated otherwise

EXAMPLE 1

A series of light-curable pastes containing a resin system and a filler system are mixed in a light-excluding mixer (Double Planetary Ross Mixer Model LDM, Charles Ross & Son, N.Y.) and formed into tapes for orthodontic adhesives. The resin system is a 50/50 blend of Bis-GMA and TEGDMA, combined with 0.25% camphorquinone and 0.5% dimethylaminophenethanol, based on the weight of the resin. The filler system formulations along with pertinent test data are shown in Table 1. The colloidal silica used is a hydrophilic, amorphous, fumed colloidal silica having a 50 $m^2/g$ particle surface area (available from Degussa Corp. under the name Aerosil TM OX-50). The $ZrO_2/SiO_2$ filler is prepared according to Example 6 in the aforesaid U.S. Pat. No. 4,503,169.

TABLE 1

| SAMPLE NUMBER | FILLER SYSTEM | | % FILLER LOADING IN PASTE | COMPRESSIVE STRENGTH (p.s.i.) | DIAMETRAL TENSILE STRENGTH (p.s.i.) | CONSISTENCY (mm) |
| --- | --- | --- | --- | --- | --- | --- |
| | WEIGHT % COLLOIDAL SILICA | WEIGHT % $ZrO_2/SiO_2$ FILLER | | | | |
| 1 | 0 | 80.00 | 80.0 | 57120 | 11613 | 27.78 |
| 2 | 2.0 | 78.00 | 80.0 | 57365 | 11332 | 28.58 |
| 3 | 2.8 | 77.20 | 80.0 | 58262 | 11487 | 31.75 |
| 4 | 4.0 | 76.00 | 80.0 | 58042 | 12176 | 39.69 |
| 5 | 4.5 | 77.80 | 82.3 | 62101 | 12049 | 25.4 |
| 6 | 8.0 | 72.00 | 80.0 | 62000 | 12467 | 46.04 |
| 7 | 10.7 | 73.20 | 83.9 | 66246 | 13526 | 36.51 |
| 8 | 13.2 | 74.80 | 88.0 | 64394 | 13664 | 28.58 |
| 9 | 21.97 | 65.93 | 87.9 | 68538 | 14030 | 28.58 |
| 10 | 32.0 | 48.00 | 80.0 | 66132 | 13312 | 43.66 |
| 11 | 40.0 | 40.00 | 80.0 | 67179 | 12641 | 39.69 |
| 12 | 48.0 | 32.00 | 80.0 | 69234 | 12804 | 26.99 |
| 13 | 52.5 | 22.50 | 75.0 | 68576 | 10468 | 32.54 |
| 14 | 56.08 | 14.02 | 70.1 | 71148 | 9831 | 42.07 |
| 15 | 62.3 | 0 | 62.3 | 68357 | 9546 | 42.86 |

In restorative applications, translucency of the cured paste is often preferred for cosmetic reasons. However, for masking severely stained teeth, a more opaque paste is preferred. Visual opacity is controlled by matching the refractive indices of the resin and the filler. The closer the refractive indices, the more translucent the cured paste. Of course, opacity is also affected by the thickness of the cured paste. That is, a cured paste may be translucent at a given thickness, but become progressively more opaque as thickness increases. Furthermore, visual opacity is reduced by removal of occluded air from the paste, e.,g., by mixing the paste under partial vacuum.

Again, depending on ultimate use, the paste is preferably radiopaque (i.e., opaque to x-rays) or radiolucent (i.e., translucent to x-rays). The amount of radiopacity can vary and is measurable by known methods, such as disclosed in the aforesaid U.S. Pat. No. 4,503,169.

Optionally, the paste used in accordance with the present invention contains reinforcing fibers such as glass or ceramic fibers. Preferably, the fibers have an index of refraction closely matching the cured resin to maintain the desired translucency, for example, in veneer or matrix tape applications. In an orthodontic bracket adhesive tape or an orthodontic bracket of the present invention, a fiber scrim is preferably imbedded in the adhesive layer.

To more fully describe the present invention, the following non-limiting examples are provided. All parts The adhesives are formed into tapes by rolling or pressing the pastes between low adhesion cover sheets. Two types of low adhesion cover sheets are used: (1) a low-density polyethylene-coated paper with a silicone release agent (Polyslick TM, General Electric) applied to the polyethylene coat and a high density polyethylene coat on the backside of the paper to prevent curling, and (2) a clay-filled kraft paper coated with a silicone release agent (Silicone Premium, General Electric). The tapes are slit into narrow widths to correspond to the bracket width. The bracket used is an American Orthodontics, Bracket No. 095-007, 100 mesh, stainless steel brazed, central. Segments are then cut to fit the bracket screen, one cover sheet is removed and the adhesive is pressed onto the bracket screen. The remaining cover sheet is removed and the bracket is pressed onto an acid etched bovine tooth. To cure the paste, an ESPE "Elipar" dental curing light is directed around the periphery of the bracket for 20 seconds. A 0.3675 mm adhesive thickness provides good adhesion requiring little or no clean-up of excess adhesive.

To determine compressive strength and diametral tensile strength, a sample of the uncured paste is placed in a 4.06 mm I.D. glass tube capped with silicone plugs in each end of the tube. The tube is placed in a test rig pressurized with air at 0.28 MPa. The test rig contains two ESPE "Elipar" dental curing lights aimed at opposing sides of the tube and mounted on a turntable which enables the lights to be rotated around the tube in a 180° arc. The light guide of each curing light is spaced 3 mm from the tube wall. While operating both curing lights simultaneously and oscillating them continuously around the tube, the tube is exposed to four 20 second curing cycles. The tube is then removed from the test rig, placed on a pair of spaced rollers, and rotated under a 110 watt "Ritter" dental operatory light at a distance of 0.6 meters for one hour. The cured sample is removed from the tube and sliced into cylinders with a diamond saw. For compressive strength testing, an 8.23 mm long cylinder is employed, and for diametral tensile strength testing, a 2.21 mm long cylinder is employed. The cylinders are stored in 37° C. distilled water for 24 hours, then tested according to ADA Specification Nos. 8 and 27.

Consistency is measured as the spread of 0.5 ml of paste sandwiched between two 10.16×10.16 cm glass plates under a 907.2 g weight. A quantity of 0.50 ml paste is delivered onto the bottom plate, then the top plate and 907.2 g weight are added. The combined mass of the top plate and the 907.2 g weight=1027+10 g. After 2 min., the spread (diameter) of the paste is measured to the nearest 0.794 mm, and 3 readings are averaged.

EXAMPLE 2

Composite matrix tapes and veneer tapes are prepared using the same resin system as in EXAMPLE 1 combined with various filler loadings. The filler used is a combination of 80% $ZrO_2/SiO_2$ (prepared as in EXAMPLE 1 of the aforesaid U.S. Pat. No. 4,503,169) and 20% colloidal silica as used in EXAMPLE 1. Four paste samples are prepared, with the following total filler loadings: Paste 1-80% loading; Paste 2-83.5% loading; Paste 3-85.1% loading; and Paste 4-86.7% loading.

Tapes are prepared using each of the four sample pastes sandwiched between a low adhesion cover sheet as described in EXAMPLE 1 and a transparent cover sheet of polyester film having a thickness of 0.0127 mm. A paste layer of 0.1225-0.245 mm thickness is obtained in each tape by rolling the sandwich with a glass jar or pressing the sandwich between glass plates. Ease of release of the paste layer from the low adhesion cover sheet is facilitated as filler loading increases.

EXAMPLE 3

A more highly loaded paste than in the previous examples is prepared. The filler system used is the same as EXAMPLE 1, but with 15% colloidal silica and 85% $ZrO_2/SiO_2$ filler. The resin system used is the same as in EXAMPLE 1. Total filler loading is 88%. The paste is found to provide a further improvement in release. Handling properties and resistance to slump are also improved. A matrix tape using this paste is prepared as in EXAMPLE 2 having a paste thickness of 0.245 mm and a polyvinylidene chloride cover film having a thickness of 0.1715 mm. The matrix tape is used for a Class II restorative filling in an extracted human tooth. A hole is cut in the tooth removing part of a side of the tooth and part of the crown. The tape is cut to a length that slightly overlaps itself when wound around the tooth and to a width of 1.0 mm. Paste is removed from the tape leaving an amount sufficient to cover and slightly overlap the hole in the side of the tooth. The tape is wrapped around the tooth such that the paste remaining on the tape covers the hole in the side of the tooth. After placement around the tooth, the paste is cured by directing the hand held curing light described in EXAMPLE 1 over the area covered by the paste for about 20 seconds. The tooth is then filled with two successive layers of the paste used to make the matrix tape, each layer being cured by exposure to the curing light for about 30 seconds. The tape is easily placed and performs well while the tooth is filled. After the final layer of paste is cured, the tape is peeled away from the restoration. A lustrous surface finish and good contacts are obtained.

EXAMPLE 4

Paste formulations used to prepare matrix tapes as in EXAMPLE 2 are evaluated as veneers. Veneers are placed on bovine teeth and are easily shaped and tapered towards the incisal edge. After curing and removal of the transparent cover sheet, the veneer surface is completely cured and lustrous, requiring no polishing.

EXAMPLE 5

Human teeth exhibiting cervical erosion are treated with tapes prepared as in EXAMPLE 2. Several applications are required to fill some eroded areas, however placement is very rapid and an excellent surface requiring no polishing is produced.

I claim:

1. A dental tape comprising a light-curable, non-toxic paste layered between two cover sheets, at least one of which releasably adheres to the paste.

2. The tape of claim 1 wherein at least one of the cover sheets is a hand-soft, transparent film.

3. The tape of claim 2 wherein the transparent film comprises polyvinylidene chloride.

4. The tape of claim 1 wherein the releasably adhering cover sheet is a hand-hard film that is opaque to light having a wavelength capable of curing the paste.

5. The tape of claim 4 wherein the opaque film adheres to the paste through a low-adhesion backsize coating.

6. The tape of claim 1 wherein at least one of the cover sheets releasably adheres to the paste through a low-adhesion backsize coating.

7. The tape of claim 1 wherein the paste comprises a filler and a photoinitiator dispersed in a resin.

8. The tape of claim 7 wherein the resin comprises Bis-GMA.

9. The tape of claim 7 wherein the photoinitiator comprises camphorquinone.

10. The tape of claim 7 wherein the filler has a Mohs hardness less than about 4.

11. The tape of claim 7 wherein the filler has a Mohs hardness less than about 3.

12. The tape of claim 7 wherein the filler comprises nonvitreous microparticles having amorphous silica microregions uniformly interspersed with crystalline, ceramic metal oxide microregions.

13. The tape of claim 12 wherein the crystalline, ceramic metal oxide microregions are radiopaque.

14. The tape of claim 7 wherein the paste is visually translucent after curing.

15. The tape of claim 7 wherein the paste further comprises fibers that have an index of refraction the same as the resin after curing.

16. The tape of claim 7 wherein the paste further comprises a fiber scrim.

17. The tape of claim 1 wherein the paste has a thickness between 0.245 and 1.225 mm 18. The tape of claim 1 wherein the paste has a thickness between about 0.25 and 0.5 mm.

19. The tape of claim 1 wherein the paste is radiopaque after curing.

20. The tape of claim 1 wherein the paste is visually translucent after curing.

21. A dental article comprising an orthodontic bracket having a base and a light-curable, non-toxic paste sandwiched between the base and a releasably adhering substrate.

22. The article of claim 21 wherein the substrate releasably adheres to the paste though a low-adhesion backsize coating.

23. The article of claim 21 wherein the paste comprises a filler and a photoinitiator dispersed in a resin.

24. The article of claim 23 wherein the resin comprises Bis-GMA.

25. The article of claim 23 wherein the photoinitiator comprises camphorquinone.

26. The article of claim 23 wherein the filler has a Mohs hardness less than about 4.

27. The article of claim 23 wherein the filler has a Mohs hardness less than about 3.

28. The article of claim 23 wherein the filler comprises non-vitreous microparticles having amorphous silica miororegions uniformly interspersed with crystalline, ceramic metal oxide microregions.

29. The article of claim 21 wherein the substrate is a flexible cover sheet.

30. The article of claim 29 wherein the cover sheet comprises a polymer selected from the group consisting of a polyester, a fluorinated polymer, and an olefin polymer.

31. The article of claim 29 wherein the cover sheet comprises a polymer-coated paper.

32. A method of making a dental reconstruction comprising the steps of:
(a) positioning a non-toxic light-curable paste carried on a transparent film on at least part of the labial surface of a tooth,
(b) shaping the film to the contour of the tooth,
(c) curing the paste with a curing light, and
(d) removing the film.

33. A method for making a dental reconstruction comprising the steps of:
(a) removing part of a tooth including a side thereof to form a cavity,
(b) positioning a non-toxic light-curable paste carried on a transparent film on the tooth such that the past forms a wall in place of the side of the tooth removed and the film encircles the tooth, passing between the tooth and any adjacent teeth,
(c) curing the paste, and
(d) filling the remainder of the cavity with a restorative material.

* * * * *

UNITED STATES PATENT AND TRADEMARK OFFICE
CERTIFICATE OF CORRECTION

PATENT NO. : 5,015,180

DATED : May 14, 1991

INVENTOR(S) : Ronald M. Randklev

It is certified that error appears in the above-identified patent and that said Letters Patent is hereby corrected as shown below:

Col. 1, line 58, "non-toxicitY" should be -- non-toxicity --.

Col. 2, line 59, insert a comma after "0.1-5.0%".

Col. 7, Line 20, "+" should be -- ± --.

Col. 7, line 59, "out" should be -- cut --.

Col. 10, line 22, "past" should be -- paste --.

Signed and Sealed this

Thirtieth Day of March, 1993

*Attest:*

STEPHEN G. KUNIN

*Attesting Officer*    *Acting Commissioner of Patents and Trademarks*